United States Patent [19]
Gibbs

[11] Patent Number: 5,085,640
[45] Date of Patent: Feb. 4, 1992

[54] NON-REUSABLE MEDICAL NEEDLE APPARATUS

[76] Inventor: Andrew H. Gibbs, 3678 S. Walton Ave., Yuba City, Calif. 95993

[21] Appl. No.: 505,925

[22] Filed: Apr. 6, 1990

[51] Int. Cl.⁵ ............................................. A61M 5/00
[52] U.S. Cl. ..................................... 604/110; 604/218
[58] Field of Search ................. 604/110, 218, 220, 187

[56] References Cited

U.S. PATENT DOCUMENTS

| | | | |
|---|---|---|---|
| 4,731,068 | 3/1988 | Hesse | 604/110 |
| 4,826,483 | 5/1989 | Molnar, IV | 604/110 |
| 4,961,728 | 10/1990 | Kosinski | 604/110 |

*Primary Examiner*—John D. Yasko
*Attorney, Agent, or Firm*—Thomas E. Schatzel

[57] ABSTRACT

Medical needle apparatus for transferring fluid includes syringe assemblies for fluid injection and phlebotomy systems for collecting blood samples. A case with an elongated cavity therein has an open end and a relatively closed end from which a hollow needle projects. An operating member fits through the open end of the case into the cavity and controls both fluid transfer and self-destruction of the apparatus after fluid transfer to prevent reuse. Plastic deformable means responsive to pressure on the operating member in a direction toward the needle renders the apparatus non-reusable after fluid transfer either by actuating needle retraction or by increasing the lateral dimension of the operating member to prevent withdrawal. The apparatus is operable with a single hand to transfer fluid and actuate deformable means without re-positioning the hand on the apparatus.

8 Claims, 10 Drawing Sheets

| CHART OF DYNAMICALLY OPERATING FEATURES AND RESIN MATERIAL PROPERTIES SPECIFICATION ||||
|---|---|---|---|
| ISOLATED PRIMARY DYNAMIC OPERATING FEATURE OF THE MEDICAL NEEDLE DEVICE | FEATURE AS ILLUSTRATED IN THE DRAWING FIGS. AND REF NUMBERS | PRIMARY THERMOPLASTIC RESIN OR ALLOY SPECIFICATION DESIRED | INJECTION MOLD OR PART FEATURES CONTRIBUTING TO PROPER DYNAMIC OPERATION OF MECHANICAL FEATURES AND ENHANCED PERFORMANCE OF MATERIAL PROPERTIES |
| BREAKING TABS | FIG. 5, REF 67<br>FIG. 6, REF 87,88<br>FIG. 24, REF 147,148<br>FIG. 36, REF 181<br>FIG. 37, REF 198<br>FIG. 38, REF 237 | FS: 9.0 - 15<br>MET: > 3.0<br>IMP: 0.2 - 1.0<br>TEN: > 6.0<br>C-YLD: 6.0 - 9.0 | REDUCED CROSS SECTIONAL DIMENSION AT THE BREAKING POINT. REDUCED SECTION CONSTITUTES PLASTIC FLOW RESTRICTION IN THE MOLD. THESE THIN SECTIONS WILL BE THE LAST TO FILL WHILE UNDER PRESSURE. CONTROLLING THE FILL SEQUENCE FROM BOTH SIDES OF THE RESTRICTION WILL RESULT IN A WELD LINE TO ENHANCE BREAKING |
| BREAKABLE INTERMEDIATE STEP POINTS | FIG. 38, REF 237<br>FIG. 56, REF 314 | FS: 9.0 - 15<br>MET: > 3.0<br>IMP: 0.2 - 1.0<br>TEN: > 6.0<br>C-YLD: 6.0 - 9.0 | REDUCED CROSS SECTIONAL DIMENSION AT THE BREAKING POINT. REDUCED SECTION CONSTITUTES PLASTIC FLOW RESTRICTION IN THE MOLD. THESE THIN SECTIONS WILL BE THE LAST TO FILL WHILE UNDER PRESSURE. CONTROLLING THE FILL SEQUENCE FROM BOTH SIDES OF THE RESTRICTION WILL RESULT IN A WELD LINE TO ENHANCE BREAKING |
| OVER-CENTER FLEXING RETRACTION MEMBERS AND REVERSIBLE MEMBERS | FIG. 6, REF 76, 77<br>FIG. 13, REF 104, 106, 108, 109<br>FIG. 24, REF 141, 142, 143, 144 | FS: 6.0 - 9.0<br>MEF: 2.0 - 2.5<br>IMP: 1.0 - 2.2<br>TEN: 4.8 - 5.2<br>C-YLD: 5.0 - 6.0 | MEMBER CROSS SECTIONAL ASPECT RATIO CHANGES ALONG THE MEMBER LENGTH TO INDUCE CONTROL OVER FLEXING SEQUENCE IS RECOMMENDED TO CONTROL INITIAL REVERSING POINTS AND/OR TIME/FORCE RELATED FUNCTIONAL ACTUATION. |
| COMPRESSIBLE FLEXIBLE TENSION MEMBERS | FIG. 43, REF 278, 279<br>FIG. 54, REF 294, 296 | FS: 6.0 - 7.0<br>MEF: < 2.0 | MINIMUM 2:1 ASPECT RATIO TO CONTROL DIRECTION OF DISPLACEMENT WHEN SUBJECTED TO COMPRESSIVE FORCE |
| RETRACTION MEMBER ENDS AT FLEXIBLE HINGE POINTS | FIG. 1, REF 79, 81, 82, 83<br>FIG. 13, REF 111, 112, 113, 114 | TEN: 4.5 - 5.5<br>MEF: 2.0 | REDUCED DIMENSION ALONG THE SMALLER AXIS OF THE MATERIAL SECTION WITH ≥ 2:1 NOMINAL ASPECT RATIO |
| DEFORMABLE RESILIANT MEMBERS | FIG. 38, REF 237 | FS: 7.5 - 10.0<br>C-YLD: 7.0 - 8.0 | NO SPECIAL DESIGN OR MOLD FEATURES NECESSARY |
| LOW FLEXIBILITY HINGE POINTS | FIG. 56, REF 310 | FS: 8.0 - 11.0<br>TEN: 5.0 - 6.0 | NO SPECIAL DESIGN OR MOLD FEATURES NECESSARY |

LEGEND:
FLEX STRENGTH (FS) EXPRESSED IN 1000 PSI
MODULUS OF ELASTICITY IN TENSION (MET) EXPRESSED IN 10,000 PSI
MODULUS OF ELASTICITY IN FLEXION (MEF) EXPRESSED IN 10,000 PSI
IMPACT STRENGTH (IMP) NOTCHED IZOD EXPRESSED IN FT-LB/IN
TENSILE STRENGTH (TEN) EXPRESSED IN 1000 PSI
COMPRESSIVE YIELD (C-YLD) 0.1% OFFSET EXPRESSED IN 1000 PSI

Fig.57

NON-REUSABLE MEDICAL NEEDLE APPARATUS

BACKGROUND OF THE INVENTION

1. Field of the Invention

This invention relates to medical needle apparatus of a non-reusable type. More specifically, it concerns syringes and phlebotomy systems that self-destruct after a single use.

2. Description of the Prior Art

The repeated use of medical needles without proper sterilization spreads many diseases including AIDS and hepatitis. Sterilization done properly requires special equipment. It is time-consuming and it can be expensive. Thus, disposable needles are frequently used.

Such syringes are increasingly documented as causing transmission of lethal diseases through accidental needle-stick injuries to administering medical personnel, laundry workers and garbage handlers. The Occupational Safety and Health Administration (OSHA) Division of the U.S. Dept. of Labor views the problem of needle-stick injuries and used syringe disposal in medical facilities substantial enough to warrant implementation of Rule 29 CFR Part 1910 which, in part, will govern approved types and use of various needle apparatus. Additionally, the World Health Organization (WHO) has gathered data concerning the incidence of disease transmission from patient to patient through the re-use of injection syringes by medical personnel in developing countries; the transmission of such lethal diseases is also well documented among the drug abuse culture in the U.S. and other developed countries. Syringe re-use in these developing countries is caused in part by the lack of available medical personnel training, and by depressed economies which support the use of reduced quantities of needed syringes, implying the re-usability of the devices. Re-use of syringes in developed countries result from use of syringes which lack single use features, or which have single-use features which may be circumvented by the user, thus allowing re-use.

Prior art has shown various attempts to satisfy the needs of the medical community through means to retract the needle following use. (Within the context of this description, "retractable" implies non-reusable since retraction disables the injection hydraulic means.) These devices usually allow the medical worker to retract the needle to the interior cavity of the syringe barrel by locking the piston to the needle hub and pulling backward until the needle is no longer exposed to cause needle-stick injuries. Recent art has shown slidable sheaths which advance forward over the exposed needle for the same reason. The devices call for the use of two hands to activate the sheath or retraction and special training to allow proficiency with the device. In the post-sheathing or post-retraction state, the syringes are longitudinally longer than the post injection state which is not desirable for disposal. The single-use attributes of retractable devices may be voluntarily circumventable, and may in fact be re-used if the retraction is not actuated.

Further, prior art has taught of means to render syringes non-reusable following a single use. These single-use devices have means to lock the piston in the syringe barrel following injection. The WHO has specific guide-lines calling for non-circumventable single-use devices; devices not requiring special training to use, and immediate actuation of the non reusable mechanism which occurs involuntarily upon beginning the injection, and very low cost of production. Prior art accomplishes certain combinations of the WHO criteria through various means, but no known prior art teaches a device which satisfactorily accomplishes all of the aforementioned criteria in a singular design.

There is a need for medical needles that can be disposed of with minimum risk to health care workers and garbage handlers. There is further need for a non-circumventable, self-destruct system for preventing re-use. Preferably, the self-destruction should be actuated immediately following, or simultaneously with fluid transfer with continued thumb pressure on an operating member in the same manner as the fluid transfer was actuated. This enables single hand operation for both fluid transfer and self-destruction. There is a further need of syringes and phlebotomy systems with a minimum number of parts and assembly so as to be extremely cost effective promoting widespread distribution and use.

Various non-reusable medical needle devices are known. Needle retraction by pulling backward on a plunger is shown in U.S. Pat. No. 4,026,287 that issued May 31, 1977 to Haller; U.S. Pat. No. 4,507,117 that issued Mar. 26, 1985 to Vining et al.; U.S. Pat. No. 4,592,744 that issued June 3, 1986 to Jagger et al.; U.S. Pat. No. 4,650,468 that issued Mar. 17, 1987 to Jennings Jr.; U.S. Pat. No. 4,675,005 that issued June 23, 1987 to De Luccia; U.S. Pat. No. 4,710,170 that issued Dec. 1, 1987 to Haber et al.; U.S. Pat. No. 4,747,829 that issued May 31, 1988 to Jacob et al.; and U.S. Pat. No. 4,747,830 that issued May 31, 1988 to Gloyer et al. U.S. Pat. No. 4,747,831 that issued May 31, 1988 to Kulli shows needle retraction by trigger release of a compressed coil spring.

Self-destruction by plugging a barrel outlet is shown by U.S. Pat. No. 4,233,975 that issued Nov. 18, 1980 to Yerman. U.S. Pat. No. 4,391,273 that issued July 5, 1983 to Chiquiar-Arias provides for a piston puncturing a wall and being retained. U.S. Pat. No. 4,687,467 that issued Aug. 18, 1987 to Cygielski provides for cutting a hole in a piston front wall. U.S. Pat. No. 4,699,614 that issued Oct. 13, 1987 to Glazier teaches detaching a piston from a shaft. U.S. Pat. No. 4,713,056 that issued Dec. 14, 1987 to Butterfield shows gripping a piston with a latching ring. French Patent No. 2,298,340 of Blanie shows impalement of a plunger on a pointed end of a barrel.

SUMMARY OF THE INVENTION

An object of the present invention is to provide a non-reusable, medical needle apparatus that can be operated with one hand for actuating fluid transfer and for rendering the apparatus non-reusable thereafter.

Another object of the invention is to provide a medical needle apparatus that can be safely disposed of and cannot be reused.

A further object of the invention is to provide plastic deformable means for rendering the apparatus non-reusable after fluid transfer.

Briefly, the present invention includes a non-reusable, medical needle apparatus for fluid transfer. The apparatus has a case with an elongated cavity therein. The case has an open end and a relatively closed end. A hollow needle projects from the closed end of the case during fluid transfer an is in fluid flow communication with the elongated cavity. An operating member has one end that fits into the cavity through the open end of the case and an opposite end that projects outwardly therefrom. Means are provided for restraining the case with two fingers of one hand while applying thumb pressure with the same hand to the outwardly projecting end of the operating member in a direction towards the case. Means responsive to thumb pressure on the operating member are provided for actuating fluid transfer. The apparatus includes plastic deformable means that are separate from the case and that are responsive to thumb pressure on the operating member for rendering the apparatus non-reusable after fluid transfer.

Advantages of the invention include a medical needle apparatus that can be operated with a single hand for actuating fluid transfer and for rendering the apparatus non-reusable thereafter, that can be safely disposed of and cannot be reused, and that includes plastic deformable means for rendering the apparatus non-reusable after fluid transfer.

These and other objects and advantages of the invention will no doubt become obvious to those of ordinary skill in the art after having read the following detailed description of the preferred embodiments which are illustrated in the various drawing figures.

IN THE DRAWING

FIG. 57 is a chart which specifies the preferred mechanical properties of thermoplastic alloys which enable the achievement of specific deformable functions in the dynamically operating components of the devices shown in FIGS. 1-56.

DETAILED DESCRIPTION OF THE PREFERRED EMBODIMENT

Figure 1:
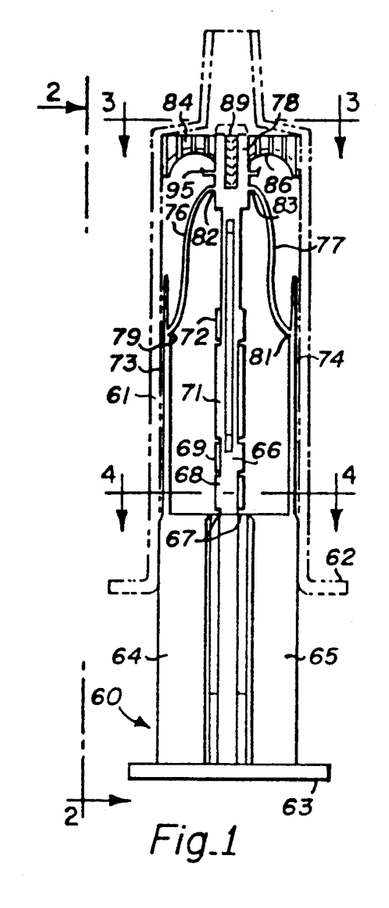
FIG. 1 is a side elevational view of a syringe plunger embodying the present invention and a syringe barrel is indicated in phantom line.
Figure 4:
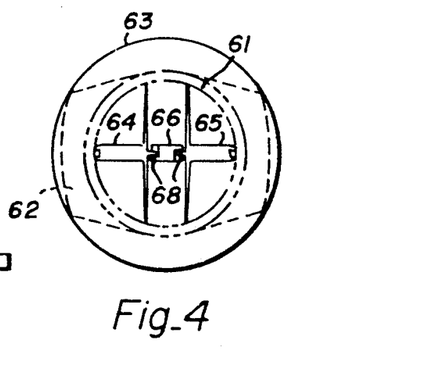
FIG. 4 is a section taken on the line 4—4 of FIG. 1.
Figures 5, 6, 7:
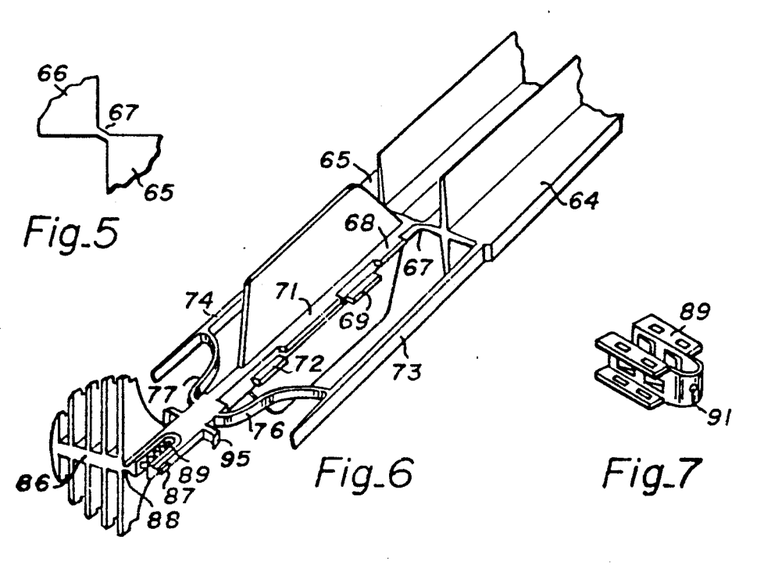
FIG. 5 is an enlarged detail view of a breaking tab between plunger sections of the syringe plunger shown in FIG. 1.
FIG. 6 is a broken perspective view of the syringe plunger shown in FIG. 1.
FIG. 7 is a perspective view of a stamped extraction grip that fits into the syringe plunger shown in FIG. 1.

Looking now at FIG. 1, a syringe plunger, indicated by general reference numeral 60, is shown in solid line, and a syringe barrel 61 having opposed finger grips 62 adjacent to the open end thereof, is shown in phantom line. The plunger is an integrally molded structure that includes a thumb rest 63 from which a pair of spaced members 64 and 65 project and support an intermediate member 66. The spaced members are connected to the intermediate member by breaking tabs 67, shown more clearly in FIG. 5. These tabs break when subjected to sufficient shear stress allowing the intermediate member to slide between the spaced members. On both sides of the intermediate member are alternatively spaced guides 68, 69, 71 and 72 (FIGS. 1, 4 and 6), defining a passage therebetween through which projecting portions of the spaced members fit upon collapse of the plunger.

Figure 2:
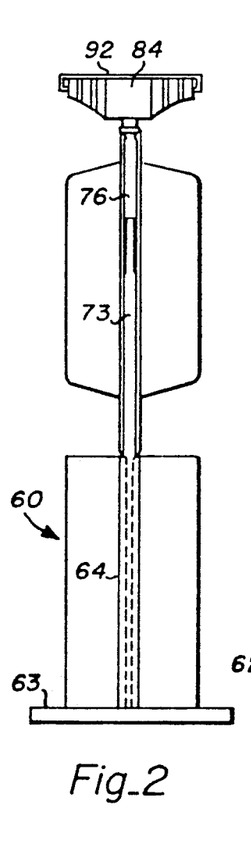
FIG. 2 is an end view of the syringe plunger without syringe barrel taken on the line 2—2 of FIG. 1.
Figure 3:
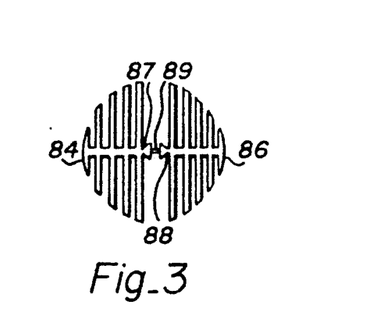
FIG. 3 is a section taken on the line 3—3 of FIG. 1, without syringe barrel.

A finger 73 extends from spaced member 64, and a finger 74 extends from spaced member 65. These fingers are connected by reversible supports 76 and 77 to a needle capture nub 78 that is an enlarged portion at the end of the intermediate member 66. Joints 79 and 81 between the reversible supports and the fingers and joints 82 and 83 between the reversible supports and the needle capture nub have reduced cross-sectional areas to provide hinge-like flexibility. Piston frame sections 84 and 86 are connected to the needle capture nub by breaking tabs 87 and 88, shown in FIGS. 3 and 6. Centered within the needle capture nub is a metal stamping 89, shown in FIGS. 1, 3, 6 and 7, having needle retaining teeth that allow a needle to pass inwardly but restrict outward movement. An opening 91 (FIG. 7) is provided in the end of the stamping to permit the needle end to pass through and be plugged by plastic in the needle capture nub. The piston frame sections, needle capture nub and metal stamping are covered by an elastomeric diaphragm seal 92, shown in FIG. 2. The barrel 61 is molded from a suitable plastic material such as polypropylene or polyethylene. The plunger 60 is singularly molded, and is shown to allow for cost efficient tooling without internal injection mold slides or pulls. The plunger is produced using a special thermoplastic alloy which will provide both the flexural properties required in the reversible supports 76 and 77, and about the joints 79, 81, 82 and 83, yet provide the low shear strength required for the breaking tabs 67, 87 and 88. Radiation sterilization of the plunger will cause polymer molecular cross-linking, resulting in a decrease in flexural properties and reduced shear strength. The use of a thermoplastic which will retain post sterilization flexural properties may also qualify for adequate retention of the breakably attached plunger components, especially when the thin-sections represented by the breaking tabs 67, 87 and 88 reflect mold details which highly restrict plastic flow within the mold. These thin section areas tend to restrict plastic flow within the mold and hence, will be the last details within the mold to be filled with plastic. As such, when material flow from opposite directions toward the breaking tabs meet under injection pressure, a "weld line" or "knit line" is formed by the meeting and plastic welding of material from either side of the tab. This will occur at a point through the center of the tab thin section, and will provide for substantially reduced shear strength. Therefore, a special alloy thermoplastic designed to function as described following radiation sterilization, or an alloy intrinsically designed to perform as molded, and gas-sterilized by using industry standard means, may be used by following common molding principals and selecting desired thermoplastic mechanical properties. The alloy will exhibit the flexural properties of polypropylene or polyethylene in the flexible supports, and will exhibit the low shear strength or material cold stress properties of acrylic in the breaking tab sections.

Figure 8:
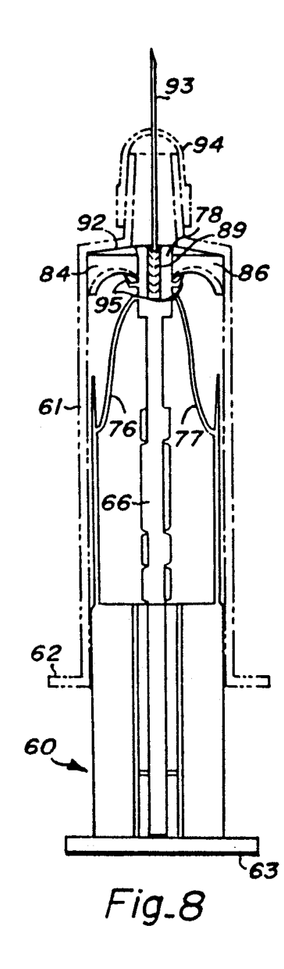
FIGS. 8-12 are operational views in sequence for the syringe plunger shown in FIG. 1.
Figure 9:
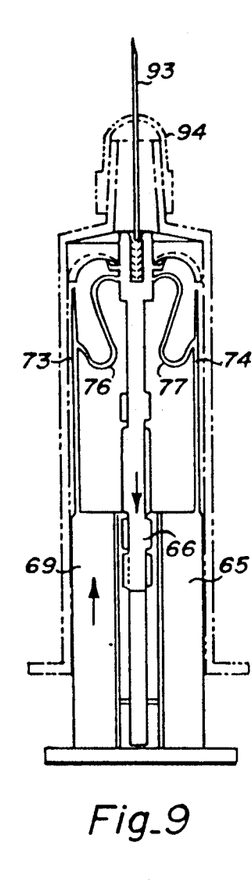
Figure 10:
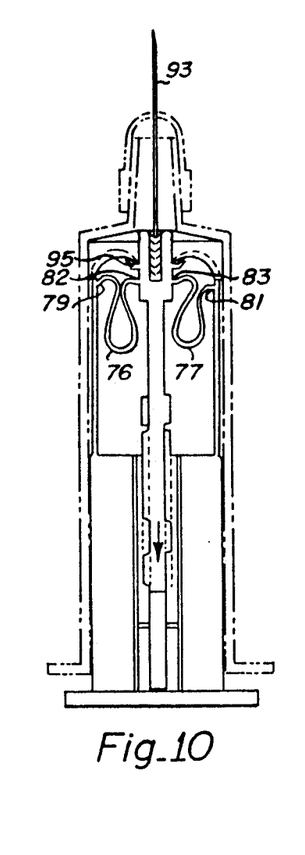
Figure 11:
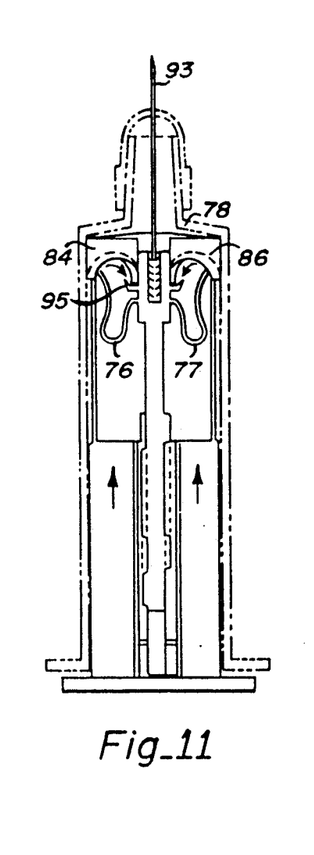
Figure 12:
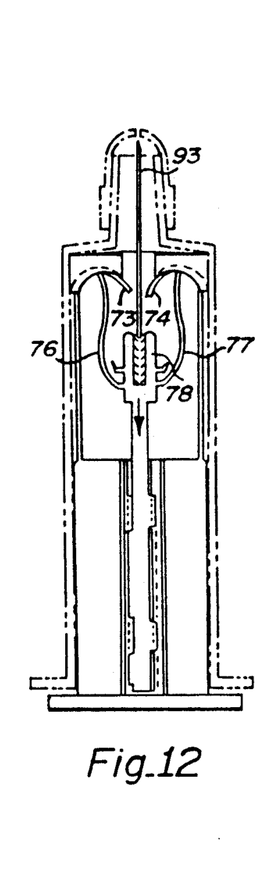

With reference to FIG. 8, a hollow needle 93 is releasably held by molded plastic or structural adhesive attachment in a forward needle hub 94. After completion of fluid injection, the end of the needle within the syringe barrel 61 punctures the elastomeric diaphragm seal 92 and is captured in the metal stamping 89. The piston frame sections 84 and 86 are restrained by the end of the syringe barrel 61, while shearing of the breaking tabs 87 and 88 (FIG. 6) allows the needle capture nub 78 to move forward relative to the piston frame and distend the elastomeric diaphragm seal. Further movement of the plunger 60 into the barrel causes the needle end to forcibly encounter the plastic needle capture nub. Sufficient impact is longitudinally induced along the hollow needle to break the mechanical bond between the needle 93 and the hub 94 allowing for subsequent needle retraction. Upon needle impact with the nub 78, further sequential movement causes the pry tabs 95 to be restrained by the piston frame sections 84 and 86, transmitting the restraining forces longitudinally through the intermediate member 66 to the breaking tabs 67. Further movement of the plunger 60 into the barrel causes the tabs 67 to break, thus allowing the intermediate member to slide between spaced members 64 and 65, as shown in FIG. 9. As the fingers 73 and 74 move forward, reversible supports 76 and 77 deform as shown. The finger tips are deflected towards the needle capture nub pry tabs 95 by concave details of the piston frame sections, thereby providing initial retraction force which removes the needle 93 rearward of its releasable attached position within the hub 94. When the reversing support joints 79, 82, 83 and 81 pass a position opposite each other, as shown in FIG. 10, a spring "over-center" mechanism results whereby the reversing supports in effort to return to their pre-stressed and relatively straight length, apply a backward force to the needle capture nub which begins to move backward from the piston frame sections, as shown in FIG. 11. The reversible supports have a resilient tendency to straighten out to their natural position as shown in FIG. 12. This forces the needle capture nub backward to where the needle 93 is fully retracted. The reversible supports retain the needle capture nub in this rearward position. This post-retraction configuration is the most compact physical size of the syringe for discarding. The entire aforementioned sequence is accomplished through the use of two finger tips located on the finger grips 62, and the thumb of the same hand which imparts uni-directional longitudinal force on the thumb rest 63 of the operating member 60.

Figures 13, 15, 16, 17:
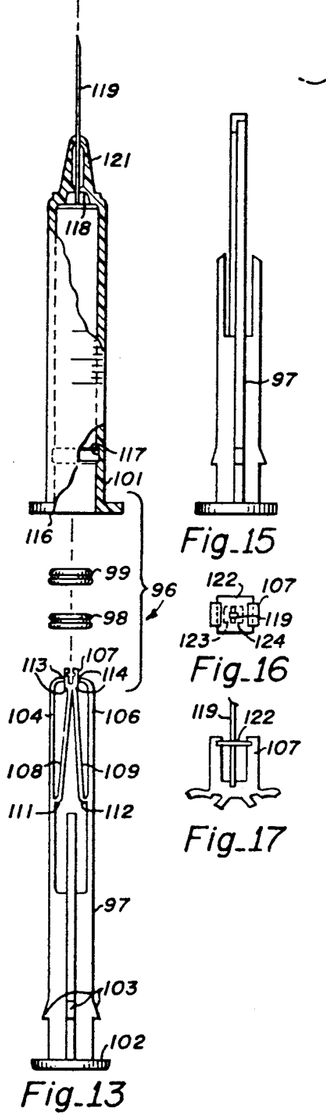
FIG. 13 is an exploded syringe assembly representing a second embodiment of the invention.
FIG. 15 is a right side view of the plunger shown in FIG. 13.
FIG. 16 is an enlarged top view of the plunger shown in FIG. 13 with needle capture plate embedded in the needle capture nub.
FIG. 17 is a fragmentary side view of the needle retraction shown in FIG. 16.
Figure 14:
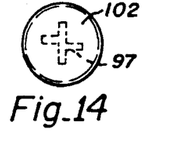
FIG. 14 is a thumb rest end view of the plunger shown in FIG. 13.

As shown in FIG. 13, a syringe assembly, indicated by general reference numeral 96, represents a second embodiment of the invention. This assembly includes a plunger 97 on which a piston frame 98 and a diaphragm 99 are fitted before insertion into a barrel 101. The plunger has at one end a thumb rest 102 and a transverse cross-sectional shape as indicated in dashed line in FIG. 14. Looking again at FIG. 13, a series of barbs 103 are located a uniform distance from the thumb rest. Outer reversible supports 104 and 106 project forward to support a needle capture nub 107. A pair of inner reversible supports 108 and 109 extend from the nub to the outer reversible supports at joints 111 and 112. Joints 113 and 114 are located between the reversible supports and the nub. All of these reversible support joints have contoured or necked-down cross-sectional areas to provide hinge-like flexibility.

Piston frame 98 is a rigid plastic piece having an internal opening for receiving the needle capture nub 107 and having concave surfaces therein to receive the convex tips of the outer reversible supports 104 and 106. The piston frame is releasably attached to the needle capture nub either by a friction fit or by matching male and female detents, either method assuring assembly of the two parts so that the surfaces proximal to the diaphragm seal 99 are co-planar with the forward surface of the frame perpendicular to the longitudinal plane of the plunger 97. Additionally, the curved surfaces of the outer reversible supports 104 and 106 are retained a distance rearward from the rear surface of the piston frame, such distance being equal to the distance the nub 107 must travel forward relative to the frame 98 to engage the needle 119 as shown in FIG. 17. An integrally molded piston frame with breaking tabs as shown in FIGS. 1, 2, 3 and 5 or FIGS. 35 and 36 may be used in lieu of the separate piston frame 98 without loss of intended dynamic operation. This configuration would represent the minimum part count for the assembly. The diaphragm 99 is made of silicone lubricated rubber (elastomeric material) and fits over the piston frame. The barrel 101 has a retaining ring or finger grips 116 at an open end thereof. A recess 117 is provided in the interior surface of the barrel for receiving the barbs 103 on the plunger. A well 118 of minimal volumetric capacity is provided at the relatively closed end of the barrel. A hollow needle 119 is releasably held by molded plastic or epoxy-type cement in a needle hub portion 121 of the barrel and projects forward from the needle hub portion and projects backward into the well where it can be captured for retraction.

FIG. 15 is a right side view of the plunger 97 shown in FIG. 13. FIG. 16 is an enlarged top view of the needle capture nub 107 with a needle capture plate 122 therein. The plate is a stamped metal insert having a pair of flaps 123 and 124 that act as anti-reversal barbs enabling the end of the needle 119 to pass through and be plugged by plastic in the needle capture nub, as shown in FIG. 17. However, the plate grips the needle sufficiently for withdrawing the needle from the needle hub portion 121 upon retraction of the needle capture nub. Both plunger 97 and barrel 101 are made of a suitable plastic such as polypropylene or polyethylene with properties described in FIG. 57.

Figure 18:
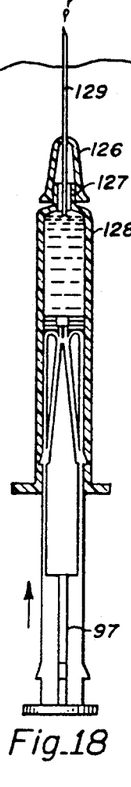
FIGS. 18-23 are operational views in sequence for the syringe assembly shown in FIG. 13.

While the needle hub portion 121 is shown integral with barrel 101, it should be understood that they can be made as separate parts. As shown in FIG. 18, a needle hub 126 fits onto a projection 127 on a barrel 128. A needle 129 is molded or cemented in the hub. This gives a doctor or nurse an option as to the size of needle desired, since the needle and needle hub can be exchanged for the desired size. Other than this modification, and the described option of using an integrally molded piston frame, the syringe assemblies shown in FIGS. 18-23 are identical with syringe assembly 96.

Figure 19:
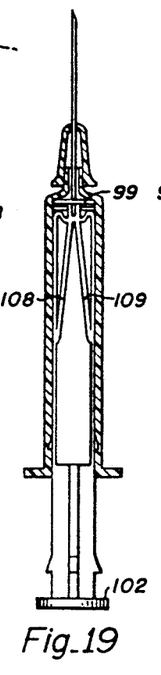
Figure 20:
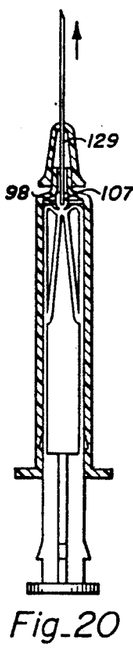
Figure 21:
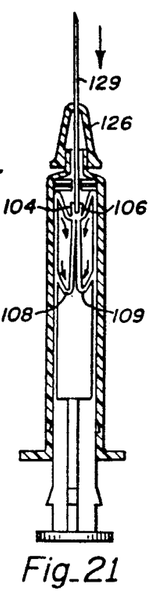
Figure 22:
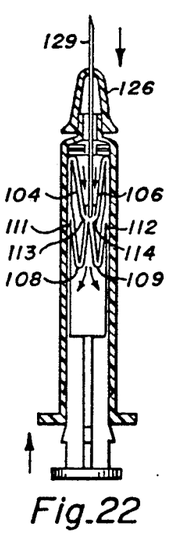
Figure 23:
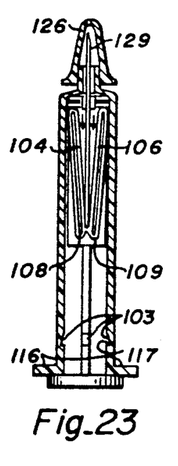

In operation, the plunger 97 is moved forward into the barrel 128, as shown in FIG. 18, to expel the fluid therein. The piston diaphragm 99 bottoms out at the end of the barrel, as shown in FIG. 19. The primary force exerted by the thumb on thumb-rest 102 is transmitted vectorially through support members 108 and 109. Continued inward force breaks the friction bond, or separates the detented assembly between the needle capture nub 107 and piston frame 98 thereby allowing the needle capture nub to move forward relative to piston frame causing the end of needle 129 to puncture diaphragm 99 and allow the needle capture nub 107 to grip the end of the needle. At this point, the curved surfaces of the outer support members 104 and 106 are in contact with the concave surfaces located on the rear of the piston frame 98 as shown in FIG. 20. Continued inward force on the plunger causes the outer reversible supports 104 and 106 to predictably and reversibly slide upon the concave surfaces on the back side of the piston frame, and inner reversible supports 108 and 109 to bend backward, retracting the needle 129 from the needle hub 126, as shown in FIG. 21. As the flexible joints 113 and 114 pass through the plane made by flexible joints 111 and 112, a spring over-center condition is produced, causing a tendency for the support members 108 and 109 to extend rearward, holding the needle in the retracted position, as shown in FIGS. 22 and 23. The barbs 103 lock within the recess 117 to lock the plunger within the barrel. This post-retraction configuration is the most compact physical size for disposal of the syringe.

The entire aforementioned sequence is accomplished through the use of two finger tips located on the finger tabs 116, and the thumb of the same hand which imparts uni-directional longitudinal force on the thumb rest 102 of the plunger 97, in a predictable sequence of a physically dynamic series of events which would appear to be almost simultaneous to the user. The present embodiment is preferably molded from polypropylene or polyethylene material. If breakable tabs and an integrally molded piston frame option is desired in lieu of the separately molded frame and plunger, then materials of a nature as described in the first embodiment and shown in FIG. 57 are preferred.

Figures 24, 25, 26, 27:
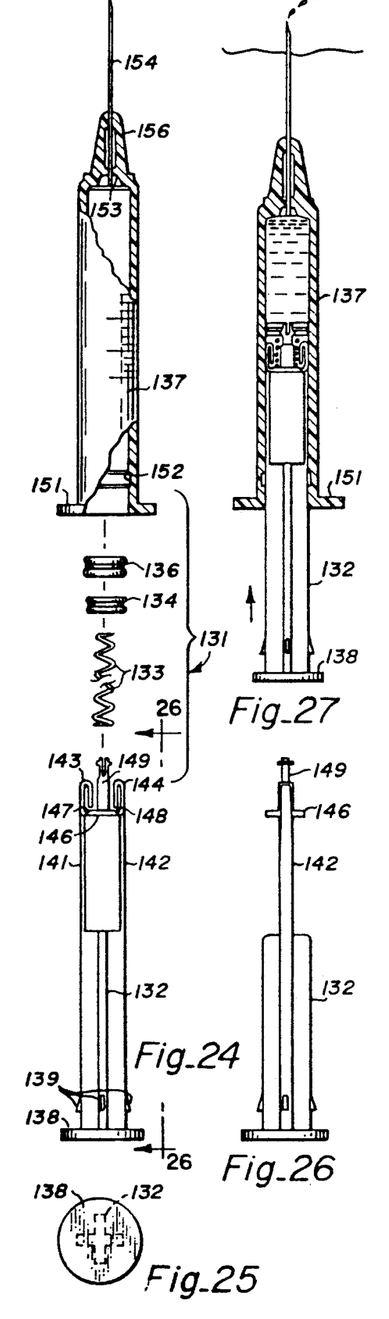
FIG. 24 is an exploded syringe assembly representing a third embodiment of the invention.
FIG. 25 is a thumb rest end view of the plunger shown in FIG. 24.
FIG. 26 is a right side view of the plunger taken in the line 26—26 of FIG. 24.
FIGS. 27-32 are operational views in sequence for the syringe assembly shown in FIG. 24.

With reference to FIG. 24, a syringe assembly, indicated by general reference numeral 131, represents a third embodiment of the invention. This assembly includes a plunger 132 on which a coil spring 133, a piston frame 134, and an elastomeric diaphragm 136 are fitted before insertion into a barrel 137. At one end of the plunger is a thumb rest 138. The plunger has a transverse cross-sectional configuration as indicated in dashed line in FIG. 25. Looking again at FIG. 24, barbs 139 project from the plunger at a uniform distance from the thumb rest. A pair of reversible supports 141 and 142 project forward lengthwise of the plunger and define an open area therebetween having a length sufficient to allow for full needle retraction. These reversible supports have leading ends 143 and 144 that bend inwardly and backwardly at an 180 degree angle, with short extensions projecting backward toward, but not connected to, a platform 146. Backward from the leading ends of the reversible supports, a platform 146 extends between the reversible supports and is connected thereto by breaking tabs 147 and 148. This platform supports an integral needle capture nub 149 that has a reverse barbed metal insert therein. FIG. 26 is a right side view of the plunger taken on the line 26—26 of FIG. 24. The coil spring is fitted about the needle capture nub and compressed when the piston frame is forced downward and locked in place about the needle capture nub. Locking of the piston frame onto the needle capture nub is achieved through outwardly projecting detents from the end of the needle capture nub and mating female details located on the interior cavity of the piston frame, assuring a specified distance between the leading ends 143 and 144 of the reversible supports and the back side of the piston frame equal to the needle capture nub travel distance required to engage the distal end of the needle. The elastomeric diaphragm is fitted over the piston frame.

The barrel 137 has a retaining ring or finger grips 151 at an open end thereof for retaining the barrel with two fingers of one hand. A recess 152 is provided in the interior surface of the barrel for receiving the barbs 139 on the plunger. A well 153 of minimum volumetric capacity is provided at a relatively closed end of the barrel. A hollow needle 154 is releasably molded or cemented in a needle hub portion 156 of the barrel. The needle projects backward into the well and forward from the needle hub portion. The needle is releasably held by the plastic or cement so that it can be withdrawn upon needle capture and retraction by the needle capture nub 149.

Figure 28:
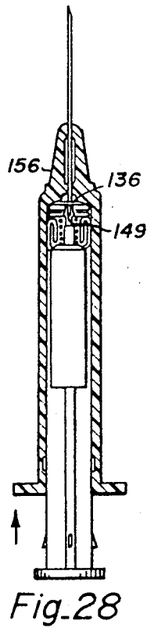
Figure 29:
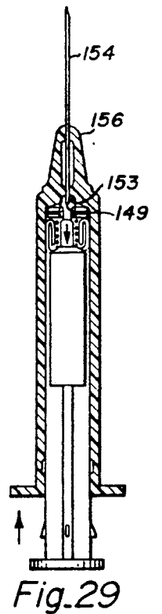
Figure 30:
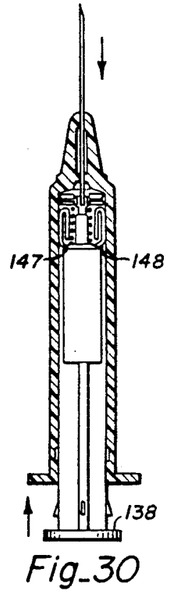
Figure 31:
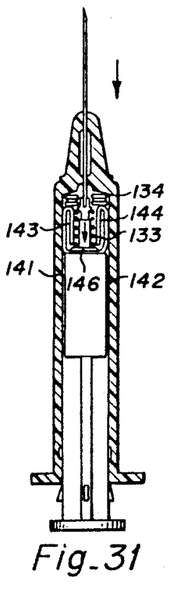
Figure 32:
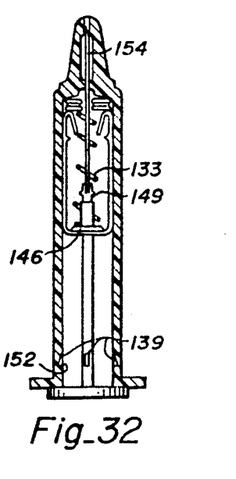

Looking now at FIG. 27, the plunger 132 is pushed forward in the barrel 137 to expel the fluid therein. Retaining ring or finger grips 151 can be held by two fingers of one hand while thumb pressure is applied to the thumb rest 138. FIG. 28 shows the piston diaphragm 136 at the end of the barrel. Continued forward movement of the plunger causes forcible separation of the mating detents between the needle capture nub 149 and the piston frame 134, allowing the needle capture nub to extend forward of the restrained piston frame, thereby stretching the diaphragm, and causing the diaphragm to be pierced by the end of the needle 154. The needle capture nub extends into the well 153 and grips the end of the needle, as shown in FIG. 29. This forward thrust produces impact that breaks a brittle type of adhesive which maintains the needle in the needle hub portion 156. Further forward movement of the plunger thumb rest causes the leading edges 143 and 144 of the reversible supports to engage the concave rear surface of the piston frame, and begin rearward travel until the free ends contact the underside of the platform 146. Continued forward movement of the plunger causes breaking tabs 147 and 148 to break, as shown in FIG. 30. Continued forward movement causes the reversible support leading ends 143 and 144 to move backwardly in a longitudinal direction opposite the reversible supports 141 and 142, thereby prying the platform 146 from its resting place in the plunger and the needle capture nub from the piston frame 134, as shown in FIG. 31. Thereafter, the coil spring 133 exerts a backward force on the platform, retracting the needle capture nub and needle, as shown in FIG. 32. Barbs 139 interlock in the barrel recess 152 to lock the plunger within the barrel. This post-retraction configuration is the most compact physical size of the syringe assembly 131 for disposal. The entire aforementioned sequence is accomplished through the use of two finger tips located on the finger tabs 151, and the thumb of the same hand which imparts uni-directional longitudinal force on the thumb rest 138 of the operating member 132, in a predictable sequence of a physically dynamic series of events which would appear to be almost simultaneous to the user. The present embodiment is preferably molded from materials of a nature as described in the first embodiment and shown in FIG. 57.

Figure 33:
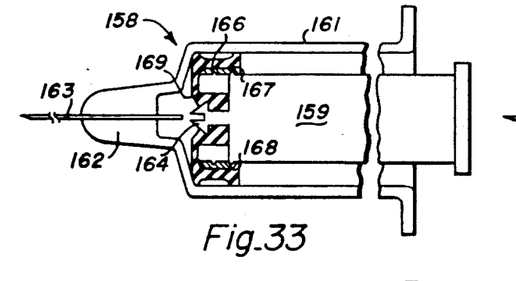
FIGS. 33 and 34 are diagrammatic operational views illustrating needle capture in a syringe assembly having a piston with a central opening therein through which a needle capture nub on a plunger fits.
Figure 34:
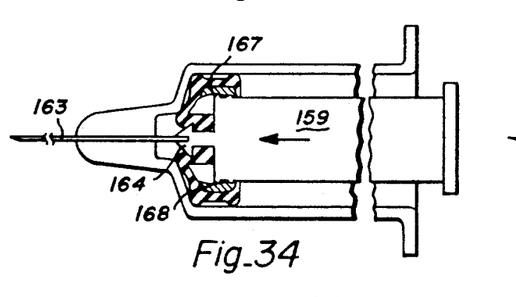

With reference to FIG. 33, a syringe assembly, indicated by general reference numeral 158, has a plunger 159 and a barrel 161. A needle hub portion 162 of the barrel holds a hollow needle 163. A needle capture nub 164 projects forward of the plunger. A piston diaphragm retaining ring 166 is held in place on the plunger by detents 167 and 168. An elastomeric diaphragm 169 fits over the piston diaphragm retaining ring and has a central opening through which the needle capture nub fits. As shown in FIG. 34, continued forward pressure on the plunger causes the detents to slip out of the retaining recesses in the piston ring, allowing the needle capture nub to move forward and grip the needle. The needle can then be retracted following separation between the piston diaphragm and the plunger. The detail of the needle capture nub 164, the piston diaphragm retaining ring 166 and piston diaphragm 167 are shown as possible alternatives to the piston end of the operating members as shown in FIGS. 1, 13 and 24. This alternate design is preferably molded from polyethylene of polypropylene thermoformed material since no material shearing or breaking between the described parts is required.

Figure 35:
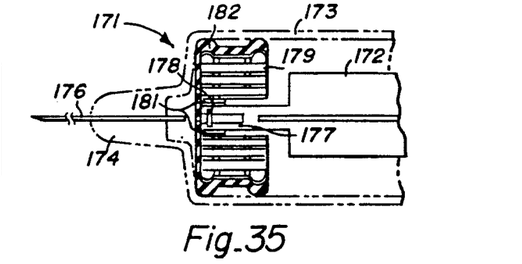
FIGS. 35 and 36 are diagrammatic operational views illustrating needle capture in a syringe assembly having a piston with an elastomeric diaphragm seal that is punctured by the needle before capture in the nub.
Figure 36:
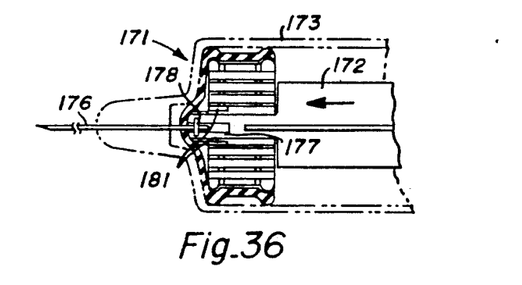

Looking now at FIG. 35, a syringe assembly, indicated by general reference numeral 171, has a plunger 172 and a barrel 173. A needle hub portion 174 of the barrel holds a hollow needle 176. A needle capture nub 177 projects forward of the plunger and has a needle capture plate 178 therein. This plate is similar to the needle capture plate 122 shown in FIGS. 16 and 17. A piston frame 179 is connected to the needle capture nub by plastic molded breaking tabs 181. This plunger 172 and piston frame 179 are molded as a single part similar to items 78 and 84 shown in FIGS. 1-6. An elastomeric diaphragm 182 fits over the piston frame and covers the needle capture nub. As shown in FIG. 36, continued forward pressure on the plunger causes rupture of the breaking tabs, allowing the needle capture nub to move forward. The diaphragm is pierced by the end of the hollow needle that is retained by the needle capture plate. Upon retraction of the needle and needle capture nub, the piston frame and diaphragm are separated from the plunger and remain in the barrel. The integrally molded piston frame and plunger shown in FIGS. 35 and 36 are preferably molded by the methods, and of the materials described in the first embodiment.

FIGS. 33-36 show piston and plunger details which are possible alternative designs to the first three embodiments. The implementation of such details are not to be limited to retraction mechanisms actuated by forward thumb pressure as described, but are additionally ideally suited for high manufacturability/low cost manually retractable medical needle devices where needle capture through the diaphragm as desired. Once the diaphragm is punctured, the device is no longer hydraulically efficient, and re-use of the device is unlikely.

Figure 37:
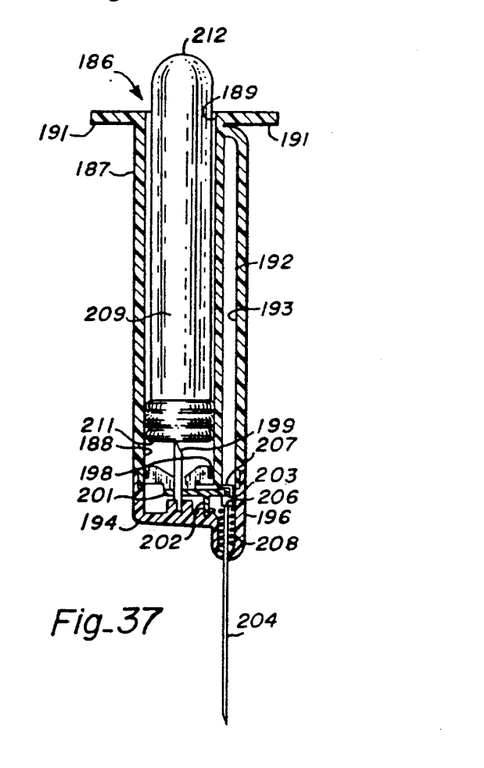
FIG. 37 is a diagrammatic view of a phlebotomy system wherein the needle and needle retaining tube are offset parallel to a blood sample collection tube.

With reference to FIG. 37, a medical needle apparatus, indicated by general reference numeral 186, is provided for phlebotomy systems in which blood samples are drawn. The apparatus includes a case or tube holder 187 having an elongated cavity 188 therein. The tube holder has an open end 189, and grips 191 are provided adjacent the open end for restraining the tube holder with two fingers of one hand. The tube holder includes a needle retaining tube 192 with a needle receiving cavity 193 therein that is parallel to the elongated cavity. The tube holder has a relatively closed end 194 defined by an end cap 196. A lever ram 197 is held in place within the elongated cavity by breaking tabs 198. A hollow perforating needle 199 is supported by the end cap and projects into the elongated cavity above the lever ram. An opening, not shown, is provided in the bottom of the perforating needle near its support in the end cap. A release lever 201 has a fulcrum 202 supported by the end cap and a retaining end 203 projecting into the needle receiving cavity. A hollow needle 204 projects from the end cap for insertion into a patient's vein and extends backward into the needle retaining tube, where a plastic molded hood 206 is provided at the opposite end of the needle. This hood has an opening 207 for receiving the retaining end of the release lever and from which blood can flow to the bottom of the perforating needle near its support in the end cap. The diameter of the hood is dimensionally close to the internal diameter of the needle retaining tube so as to prevent blood flow into the cavity, but not so close a fit as to prevent the hood and needle from slideably passing into the tube during needle retraction. A coil spring 208 is held in a compressed state within the needle receiving cavity for retracting the needle 204 into the needle retaining tube upon removal of the retaining end of the release lever from the opening in the molded hood.

An operating member in the form of a blood sample collection tube 209, preferably of the vacuum vial type, has a rubber stopper or diaphragm seal 211 at an end inserted into the elongated cavity 188 of the tube holder 187. The seal makes light contact with the perforating needle 199. An opposite end 212 of the tube projects outwardly from the tube holder.

In operation, the entire apparatus 186 is directed towards the patient and venipuncture is accomplished by inserting the needle 204 into the patient's vein. The tube holder 187 can be restrained by two fingers of one hand contacting the grip 191, while thumb pressure can be applied to the tube end 212. When the perforating needle 199 punctures the rubber diaphragm seal 211, blood flows from the patient's vein through the needle 204, through the plastic molded hood 206, over the end cap 196 to the bottom of the perforating needle, and through the perforating needle into the blood sample collection tube 209. Once the desired sample amount is collected in the tube, additional samples can be collected without removing the needle 204 from the patient's vein by simply changing blood sample collection tubes. If no further samples are desired, the medical needle apparatus is removed from the patient's vein. The tube is further depressed breaking the tabs 198 on the lever ram 197, causing it to depress the release lever 201. The retaining end 203 pivots upwardly and is removed from the molded plastic hood, allowing the needle 204 to be propelled by the spring 208 upwardly into the needle retaining tube where it is permanently retained.

Figures 38, 39, 40, 41, 42:
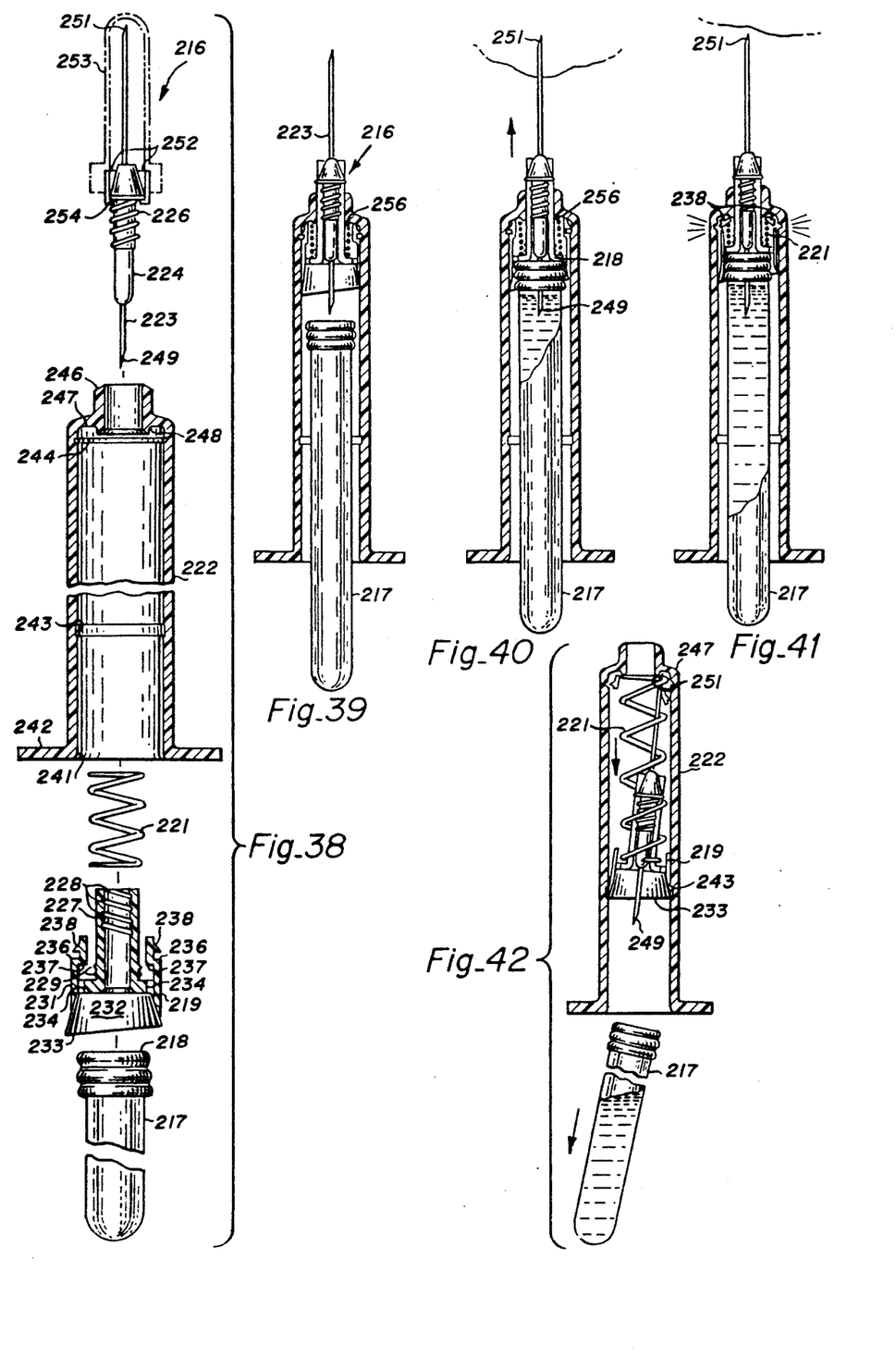
FIG. 38 is an exploded assembly view of a phlebotomy assembly wherein the needle is coaxial with the assembly.
FIGS. 39-42 are operational views of the phlebotomy assembly shown in FIG. 38.

Looking now at FIG. 38, a medical needle apparatus, indicated by general reference numeral 216, is provided as a phlebotomy system used to collect blood samples. A conventional blood sample collection tube 217, preferably of a standard vacuum type such as a 13 mm or 16 mm Vacutainer, having a rubber stopper 218 is used as an operating member for the apparatus. A case or tube holder is formed by a needle holder 219, a compression spring 221 and a barrel 222. A hollow needle 223 has a hub 224 with an externally threaded portion 226 that interfits with the needle holder. The hollow needle and hub assembly are of the currently available industry standard type, and are available in a variety of needle gauge diameters. No modification of current industry standards regarding the needle and hub are recommended.

The needle holder 219 has a sleeve 227 with internal threads 228 for receiving the externally threaded portion 226 of the needle hub 224. The outside diameter of the sleeve is slightly less than the inside diameter of the helical coil compression spring 221 so that the spring slips about the sleeve but is retained thereon by detents 229 of a slightly larger external diameter. A flange 231 extends radially from the sleeve and supports a skirt 232 that is flared and tapered to a skewed edge 233. A plurality of holes 234 are provided in the flange. The purpose of the holes are two fold; they provide a means of inexpensively molding the internal details of the catches 238, and they provide means for automatically loading the holder 219 into the barrel during the manufacturing process. Extending upwardly from the flange are a plurality of eccentric suspenders 236 that form seats 237 above the holes and that have catches 238 near their upper ends. The needle holder is preferably molded of polypropylene or polyethylene to assure the flexibility of the tapered, skewed edge 233, and to allow for permanent plastic deformation of the suspenders connecting the catches 238 to the seats 237 to allow spring expansion, but the holder can be molded of a higher density polymer with low shear strength (FIG. 57) allowing the suspenders to break, thereby separating the catches and seats allowing for spring expansion.

The barrel 222 has an open end 241, and a pair of finger grips or a retainer ring 242 extends radially outward from the open end of the barrel. A groove 243 is provided in the interior surface of the barrel for engaging the skewed edge 233 of the needle holder 219 after needle retraction. A retaining channel 244 is provided in the interior surface of the barrel for receiving the catches 238 of the needle holder upon assembly. The barrel has a neck portion 246 and a shoulder portion 247 that define a ring groove 248 on the interior of the barrel for seating the compression spring 221.

Assembly of the spring 221, needle holder 219 and barrel 222 is accomplished by slipping the spring about the sleeve 227 until the detents 229 retain the spring. A plunger having prongs that fit through holes 234 and engage seats 237 is used to insert the needle holder and spring through the barrel until catches 238 lock securely in the retaining channel 244. As the spring is being compressed it will center on and be retained by the ring groove 248. The sleeve will slide through the barrel neck portion 246 and extend slightly beyond when the needle holder is attached to the barrel.

Hollow needle 223 has an end 249 for puncturing the rubber stopper 218 of the blood sample collection tube 217 and an end 251 for insertion into a patient's vein. The needle hub 224 has wings 252 that interlock with a needle protection cap 253, shown in phantom line, and that serve to assist turning the hub. A protection cap, not shown, is provided for the stopper end of the needle and is removed by turning the hub. The hub is also turned for insertion into the sleeve 227 of the needle holder 219. As the hub approaches its final tightened position, the cap 253 contacts the end of the needle holder sleeve and causes barbs 254 on the underside of the cap to spread, thereby causing the release of the cap from the hub. The cap 253 is color-coded per industry standards to indicate needle gauge.

In operation, the medical needle apparatus 216 is assembled as shown in FIG. 39 and ready for use. A case or tube holder 256 has the hollow needle 223 mounted therein and a blood sample collection tube 217 is loosely fitted into the tube holder. As shown in FIG. 40, the needle end 251 is inserted into a patient for drawing blood and the collection tube that acts as an operating member is pushed forward in the tube holder so that the needle end 249 pierces the stopper 218. The blood pressure differential between the patient and the collection tube causes blood to flow through the hollow needle into the tube. Once the collection tube is filled to the desired level, additional samples can be drawn without removing the needle end 251 from the patient by simply changing collection tubes. If no further samples are desired, the needle end 251 is removed from the patient, as shown in FIG. 41, and the collection tube is immediately forced forward towards the needle, causing the eccentric suspenders 236 to break at the joints above seats 237. This causes separation of the catches 238 from the needle holder and frees the compression spring 221. If polypropylene or polyethylene material is used for the needle holder, the forward action causes the suspenders to permanently deform thereby freeing the compression spring. The spring expands, as shown in FIG. 42, pushing the needle holder 219 and collection tube backward, retracting the needle. The skewed edge 233 engages the groove 243 and locks the needle holder therein. The collection tube is manually removed from the needle end 249. Since the groove 243 is diametrical, while the skewed edge is inclined, the needle holder is tilted so that end 251 is positioned against the barrel shoulder portion 247. The entire needle 223 is locked within the barrel 222 to avoid post-procedure needle stick injuries.

Both the blood collection and retraction actuation processes are accomplished with the use of two fingers and the thumb of a single hand. Only the removal of the tube 217 from the case, needle, holder assembly requires the use of a second hand, and this only after the exposed surfaces of the needle are safely retracted within the holder.

Figure 43:
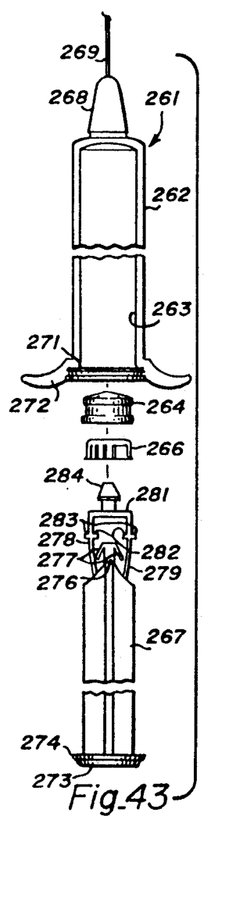
FIG. 43 is an exploded assembly view of a syringe that is rendered non-reusable after fluid transfer.

Another embodiment of the invention, shown in FIG. 43, is a medical needle apparatus in the form of a syringe assembly, indicated by general reference numeral 261. This assembly includes a syringe barrel 262 having an elongated cavity 263 therein. An elastomeric piston 264 and a spring toothed collar 266 are mounted on a plunger 267 and inserted into the elongated cavity in the syringe barrel. The syringe assembly can be filled with fluid for injection but is rendered non-reusable upon start of the fluid injection process.

The syringe barrel 262 has a needle hub 268 with a hollow needle 269 projecting therefrom. The needle is in fluid flow communication with the elongated cavity 263. The opposite end of the syringe barrel is open and a circumferential socket 271 extends thereabout. A pair of finger grips 272 extend outwardly from the open end of the barrel for restraining the barrel with two fingers of one hand while applying thumb pressure to the plunger.

The plunger 267 has a thumb rest 273 at one end and a circumferential projection 274 is provided thereon for fitting into the socket 271 of the syringe barrel 262. The plunger is a whole piece molded of polymer plastic, preferably polyethylene or polypropylene. Wedging surfaces 276 and resilient locking wings 277 extend in planes transverse relative to each other. A pair of flexible straps 278 and 279 are joined to a collar support 281 having inner shoulders 282 and outer shoulders 283. A piston holder 284 projects from the collar support at the other end of the plunger.

Figure 44:
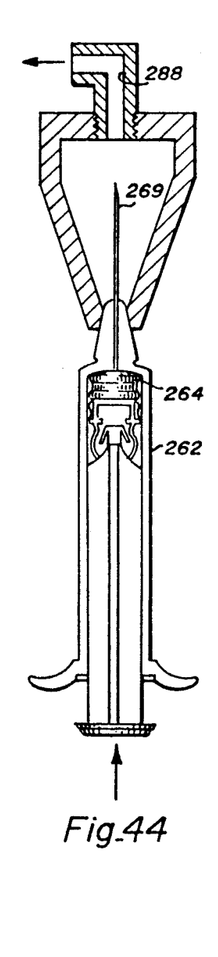
FIGS. 44-48 are operational views in sequence for the syringe assembly shown in FIG. 43.
Figures 49, 50, 51, 52:
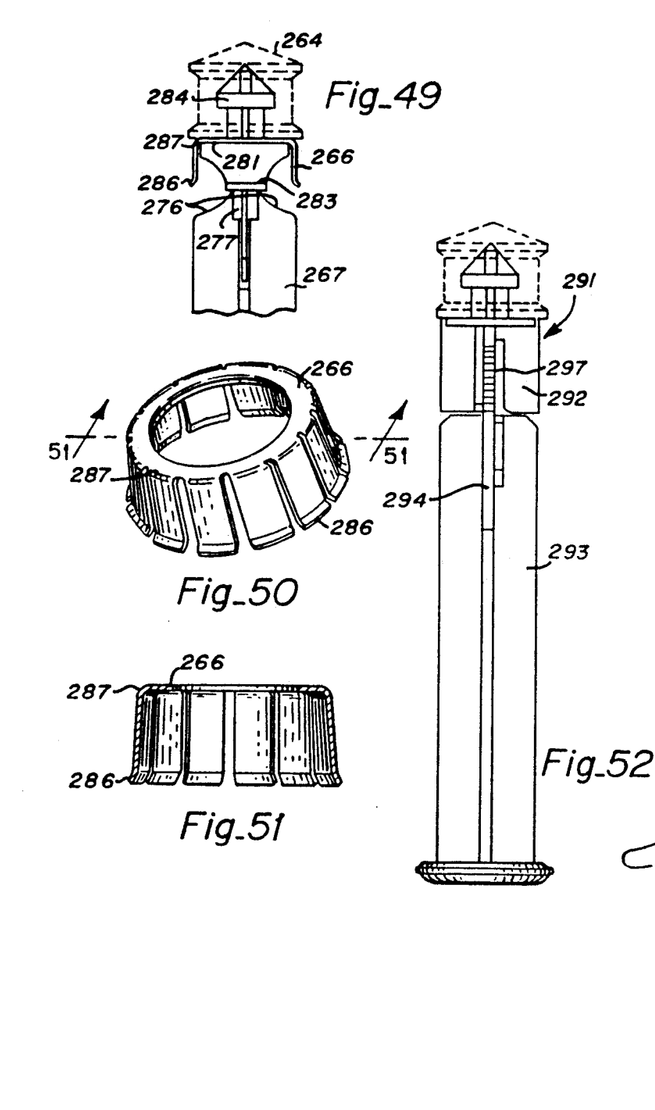
FIG. 49 is an enlarged fragmentary portion of the syringe plunger assembly shown in FIG. 43.
FIG. 50 is a perspective view of an anti-reversal spring toothed collar shown in FIGS. 43 and 49.
FIG. 51 is a section taken on the line 51 51 of FIG. 50.
FIG. 52 is a side view of a plunger that interlocks with a syringe barrel to prevent secondary plunger retraction.

The plunger 267, spring toothed collar 266 and elastomeric piston 264 are assembled as shown in FIG. 49. The spring toothed collar, shown more clearly in FIGS. 50 and 51, has outwardly flared edges 286. These edges contact the outer shoulders 283 to locate the seated position of the collar on the collar support 281. A tapered edge 287 is provided at the opposite end of the spring teeth. When the collar is press-fit installed, these tapered edges irreversibly grab the diameter of the collar support. The elastomeric piston fits onto the piston holder 284. The plunger assembly is inserted into the syringe barrel 262 at the manufacturing site, as shown in FIG. 44, and the piston is drawn towards the hollow needle 269 by applying a negative pressure to the needle from a vacuum source 288.

Figure 45:
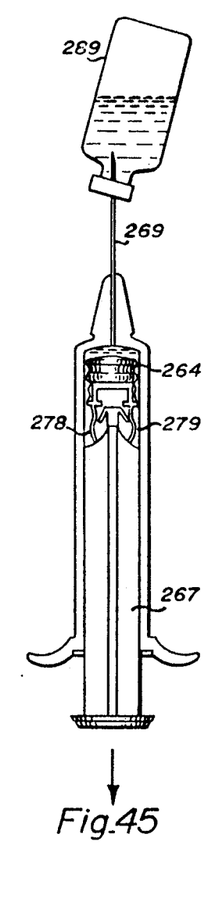
Figures 46, 47:
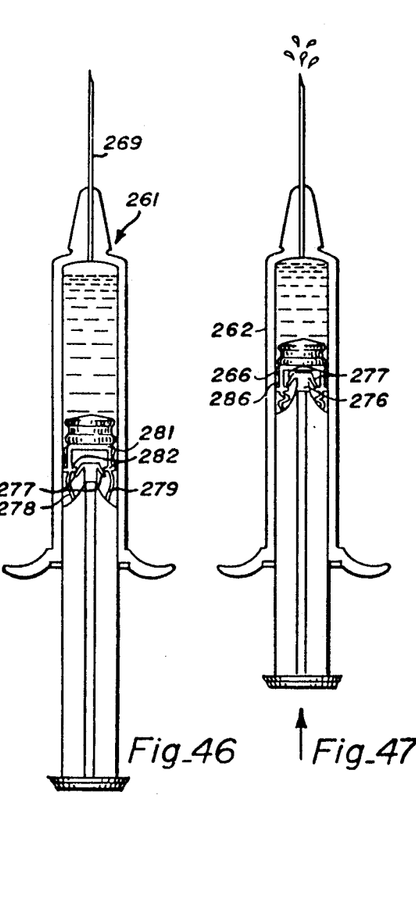
Figure 48:
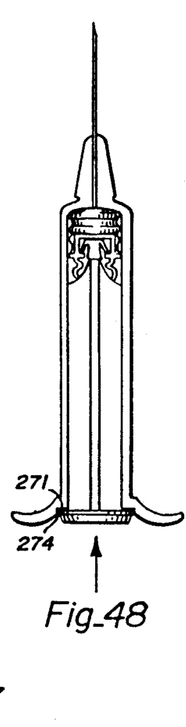

In operation, the syringe barrel 262 can be filled with fluid by inserting the needle 269 into a fluid source 289, as shown in FIG. 45, and drawing backward on the plunger 267. During this stage, the flexible straps 278 and 279 are stressed in tension and the elastomeric piston 264 follows the plunger as it is withdrawn. When a desired volume of fluid is obtained in the syringe barrel, the volume can be checked. Now the syringe assembly 261 is ready for injection, as shown in FIG. 46. The plunger is pushed forward slightly towards the needle and when exposed to increased hydraulic pressure within the barrel, straps 278 and 279 are stressed in compression causing them to buckle. As the resilient locking wings 277 contact the inner shoulders 282 of the collar support 281, the wings deflect inwardly so as to slip by the shoulders. continued thumb pressure causes the wings to slip past the shoulders and snap open, firmly locking the plunger and collar support together as shown in FIG. 47. Simultaneously, the wedging surfaces 276 (both shown in FIG. 49) contact the interior of the spring toothed collar 266 causing the outwardly flared edges 286 to expand and cut into the interior of the syringe barrel. At this point, the plunger cannot be withdrawn but injection can proceed. At the completion of injection, as shown in FIG. 48, the circumferential projection 274 snaps into the circumferential groove 271 locking the plunger within the syringe barrel in conjunction with the laterally expanding spring tooth collar to prevent prying of the plunger therefrom. Once the injection is started, the anti-reversal features of the assembly cannot be circumvented, and the syringe device becomes non-reusable for subsequent injections.

The entire aforementioned sequence is accomplished through the use of two finger tips located on the finger tabs 271, and the thumb of the same hand which imparts uni-directional longitudinal force on the thumb rest 273 of the operating member 267 in a predictable sequence of a physically dynamic series of events which would appear to be almost involuntarily simultaneous to the user during the injection cycle.

Figure 53:
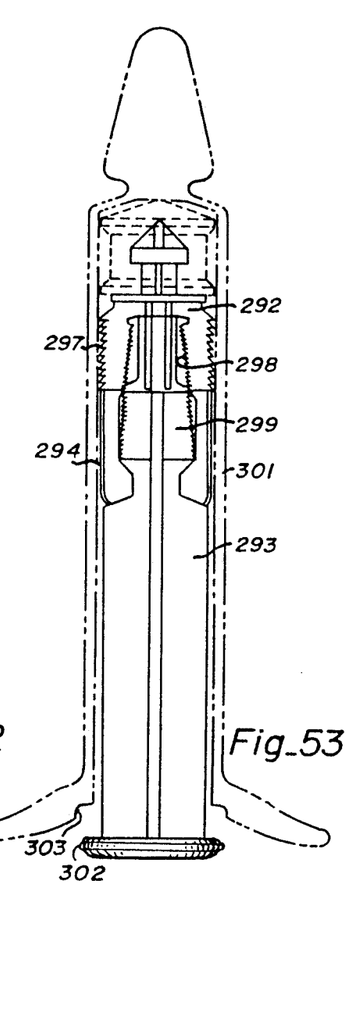
FIG. 53 is a front view of the plunger shown in FIG. 52 with a syringe barrel indicated in phantom line.
Figure 54:
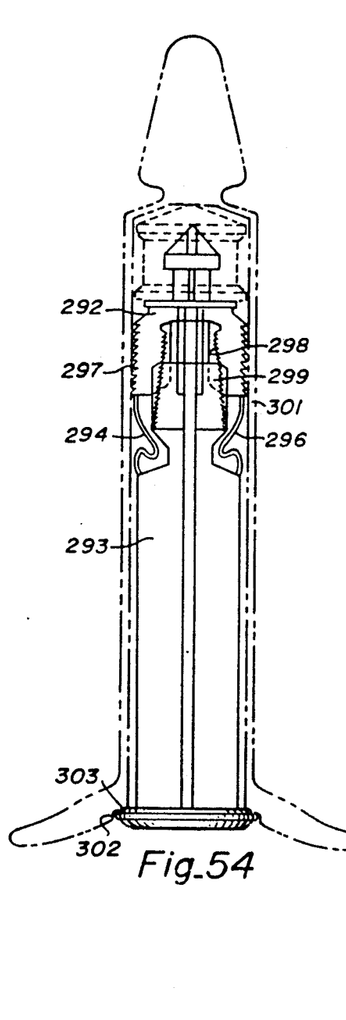
FIG. 54 is a view similar to FIG. 53 but with the plunger locked within the syringe barrel.

With reference to FIGS. 52-54, a further embodiment of the invention is represented by a plunger, indicated by general reference numeral 291. This plunger has a forward portion 292 and a rearward portion 293 that are joined together by flexible straps 294 and 296. Anti-reversing teeth 297 are integrally molded on the outer surfaces of the forward portion of the plunger. This forward portion has an opening 298 with internal teeth for receiving an externally toothed projection 299 from the rearward portion. The flexible straps buckle when subjected to compressive stress, as shown in FIG. 54. As the rearward projection is forced into the forward portion opening, the forward portion expands laterally and the anti-reversing teeth engage the interior surface of a syringe barrel 301. The anti-reversing teeth are made of a higher density polymer than the syringe barrel so that tooth engagement can be realized. A circumferential projection 302 on a thumb rest of the plunger snaps into a circumferential groove 303 at the open end of the syringe barrel to lock the plunger therein as shown in FIG. 54. This locking, in conjunction with the laterally expanding anti-reversal teeth, prevents prying of the plunger from the syringe barrel.

Figure 55:
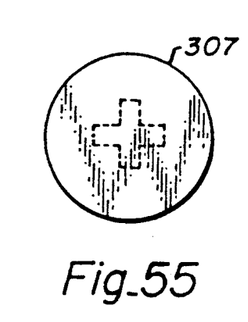
FIG. 55 is a thumb rest end view of a plunger.
Figure 56:
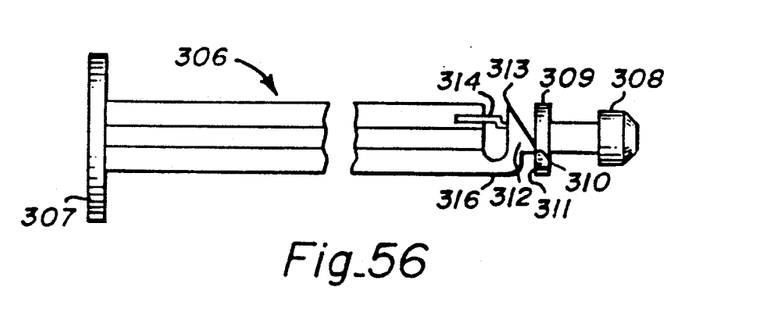
FIG. 56 is a side view of the plunger shown in FIG. 55 having an anti-reversing barb for preventing secondary plunger retraction.

Looking now at FIGS. 55 and 56, an additional embodiment of the invention is represented by the plunger, indicated by general reference numeral 306. This plunger is particularly suitable for syringe barrels having a small bore. A thumb-rest 307 is provided at one end of the plunger, and the transverse cross-sectional shape of the plunger is as indicated by dashed lines in FIG. 55. At the other end of the plunger is a piston holder 308 for receiving an elastomeric piston, not shown. The piston holder is joined to a collar 309 having a fixed barb 311 on one side thereof. An anti-reversing barb 312 is connected at hinge 310 to the collar. The anti-reversing barb has a barb point 313 facing the opposite side of the collar from the fixed barb. An eccentrically stepped tension strap 314 supports the anti-reversing barb near the barb point and an elbow 316 supports the opposite side of the anti-reversing barb so that tension can be transmitted through both the tension strap and the elbow. This enables the plunger to be withdrawn once for filling a syringe. Upon increased internal hydraulic pressure realized at the start of the injection, the tension strap is subjected to compressive stress and breaks at the intermediate step point. Compressive force is transmitted to the reversing barb through the elbow causing the barb point 313 to pivot backwardly and laterally inward. Upon secondary retraction of the plunger, only the elbow is tensioned, causing the barb to pivot at the hinge towards the collar so that the barb point moves forward and laterally outward thereby preventing secondary withdrawal of the plunger once the injection, or downward stroke of the plunger has commenced. The plunger is assembled into the barrel using differential pressure means shown in FIG. 44. The breakable intermediate step point which is intended to break on the plunger down-stroke upon realization of increased internal hydraulic pressure, is designed in the same method as described in the first embodiment whereby the restricted plastic flow through the thin section causes the predictable relative "knit line" or "weld line" weakening of an otherwise resilient molded polymer FIG. 57.

The obvious interpretation of the non-retraction barb is that actuation will cause the sharpened barb to pierce the interior surface of the barrel, but a circumferentially expanding friction lock in lieu of barb point penetration may be used.

The present embodiment, since it is applicable to existing, unmodified syringe barrels, can utilize existing elastomeric piston seals, and requires only modification of the piston end of the plunger as shown in FIG. 55, and requiring no additional part count, is absolutely the least expensive method of employing non-circumventable, non-reusable features in a syringe.

The entire aforementioned sequences shown in FIGS. 43-56 are accomplished through the use of two finger tips located on the finger tabs, and the thumb of the same hand which imparts uni-directional longitudinal force on the thumb rest of the operating member in a predictable sequence of a physically dynamic series of events which would appear to be almost involuntarily simultaneous to the user during the injection cycle. The user is not required to use the present inventions in any way different from the method of use currently employed during the use of presently available syringe devices, and need not be re-trained on the use of the present invention. The dynamic operation of the parts of the present invention are specifically intended to actuate the intended functional details of the devices with no conscious or voluntary effort on the part of the user.

With reference to FIG. 57, this chart specifies the preferred mechanical properties of thermoplastic alloys enabling the achievement of specific deformable functions of the dynamically operating components of the apparatus shown in FIGS. 1-56. Disposable medical needle devices are primarily manufactured using injection moldable plastic resins and employ static design principles to the individual components of the devices. The mechanical engineering properties of the commonly used materials such as polypropylene and polyethylene are well known. When the use of commodity priced or FDA approved resins will impede the intended dynamic operation of the devices, an alloy of various ratios of the common resins will provide the desired mechanical properties which will assure predictable deformation. Since 1985, the number of specific purpose resin alloys has increased by over 8000. Currently, over 9000 alloys exist. A plurality of alloys are therefore likely to perform the intended functions. The static and dynamic functions of the devices specifically and primarily employ tensile, shear, compression, impact and flexural characteristics of thermoplastic resins and resin alloys.

From the foregoing description, it will be seen that various medical needle apparatus for fluid transfer have been disclosed. Such apparatus includes a case with an elongated cavity therein. The case has an open end and a relatively closed end. A hollow needle projects from the closed end of the case during fluid transfer and is in fluid flow communication with the elongated cavity. An operating member has one end that fits into the cavity through the open end of the case and an opposite end that projects outwardly therefrom. Means are provided for restraining the case with two fingers of one hand while applying thumb pressure with the thumb of the same hand to the outwardly projecting end of the operating member in a direction towards the case. Means responsive to thumb pressure on the operating member are provided for actuating fluid transfer. The apparatus includes plastic deformable means that are separate from the case and that are specifically designed to perform the intended dynamic functions based on function dictated engineering properties of certain molded thermoplastic alloys, and that are responsive to thumb pressure on the operating member for rendering the apparatus unusable after fluid transfer.

Although the present invention has been described in terms of the presently preferred embodiments, it is to be understood that such disclosure is not to be interpreted as limiting. Various alterations and modifications based on plastic deformation will no doubt become apparent to those skilled in the art after having read the above disclosure. Accordingly, it is intended that the appended claims be interpreted as covering all alterations and modifications as fall within the true spirit and scope of the invention

What is claimed is:

1. A non-reusable medical needle apparatus for transferring fluid, said apparatus comprising:
    a case with an elongated cavity therein, said case having an open end and a relatively closed end,
    a hollow needle projecting from the closed end of the case during fluid transfer, said needle being in fluid flow communication with the elongated cavity,
    an operating member having one end fitting into the cavity through the open end of the case and having an opposite end projecting outwardly therefrom,
    means for restraining the case with two fingers of one hand while applying thumb pressure with the same hand to the outwardly projecting end of the operating member in a direction towards the case,
    means responsive to thumb pressure on the operating member for actuating fluid transfer, and
    integrally molded plastic means that deforms in response to thumb pressure on the operating member for rendering the apparatus non-reusable after fluid transfer, said plastic means being separate from the case.

2. A non-reusable syringe for injecting fluid, said syringe comprising:

a barrell with elongated cavity therein, said barrel having an open end and a relatively closed end, a hollow needle projecting from the closed end of the barrel, said needle being in fluid flow communication with the elongated cavity, plunger fitting into the open end of the barrel and having an end projecting outwardly therefrom, said plunger having a lateral dimension enabling plunger withdrawal once for filling the barrel with fluid, means for restraining the barrel with two fingers of one hand while applying thumb pressure with the same hand to the outwardly projecting plunger end in a direction towards the barrel, means responsive to thumb pressure on the plunger for injecting fluid, and integrally molded plastic means that deforms in response to thumb pressure on the plunger for increasing the lateral dimension of the plunger to interlock with the barrel thereby preventing secondary plunger withdrawal and rendering the syringe non-reusable after fluid injection.

3. The medical needle apparatus of claim 1, further including means for locking the operating member in a position fully inserted into the case, said locking means coacting between the operating member and the case.

4. The medical needle apparatus of claim 2 wherein said plunger includes an anti-reversal spring toothed collar fitted about the plastic means to be expanded laterally thereby.

5. The medical needle apparatus of claim 2 wherein said plunger includes integrally molded anti-reversing teeth of a higher density polymer than the barrel so that tooth engagement can be realized.

6. The medical need apparatus of claim 2 wherein said integrally molded plastic means is part of the plunger, said plastic means including two portions interconnected by a plurality of flexible straps than bend in compression during fluid injection allowing one portion to fit within the other portion thereby spreading the other portion for increasing the lateral dimension of the plunger.

7. The medical needle apparatus of claim 2 wherein said integrally molded plastic means is part of the plunger, said plastic means including a hingedly mounted anti-reversing barb, and a strap that supports the barb during initial plunger withdrawal, but is breakable in response to thumb pressure on the plunger allowing the barb to pivot in response to plunger reversing thereby increasing the lateral dimension of the plunger to interlock with the barrel.

8. A non-reusable syringe for injecting fluid, said syringe comprising:

a barrel with an elongated cavity therein, said barrel having an open end and a relatively closed end, a hollow needle projecting from the closed end of the barrel, said needle being in fluid flow communication with the elongated cavity, a plunger fitting into the open end of the barrel and having an end projecting outwardly therefrom, said plunger having a lateral dimension enabling plunger withdrawal once for filling the barrel with fluid, means for restraining the barrel with two fingers of one hand while applying thumb pressure with the same hand to the outwardly projecting plunger end in a direction towards the barrel, means responsive to thumb pressure on the plunger for injecting fluid, and plastic deformable means responsive to thumb pressure on the plunger for increasing the lateral dimension of the plunger to interlock with the barrel and thereby render the syringe non-reusable after fluid injection by preventing secondary plunger withdrawal, said plastic deformable means being formed by two plunger portions interconnected by integrally molded flexible straps that bend in compression during injection so that the two plunger portions can interlock and wedge within the barrel.

* * * * *